US006706889B1

(12) United States Patent
Stern et al.

(10) Patent No.: US 6,706,889 B1
(45) Date of Patent: Mar. 16, 2004

(54) DINITROPYRAZOLOPYRAZOLE-AMINE SALTS USEFUL IN GUN PROPELLANTS

(75) Inventors: Alfred G. Stern, Upper Marlboro, MD (US); Jesse S. Moran, King George, VA (US); R. Jason Jouet, Washington, DC (US); Michael E. Sitzman, Adelphi, MD (US); Philip F. Pagoria, Livermore, CA (US); Gregory S. Lee, San Ramon, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 36 days.

(21) Appl. No.: 10/326,964

(22) Filed: Dec. 20, 2002

(51) Int. Cl.$^7$ ............................................. C07D 231/54
(52) U.S. Cl. .................................................. 548/360.5
(58) Field of Search ....................................... 548/360.5

(56) References Cited

U.S. PATENT DOCUMENTS

| | | | |
|---|---|---|---|
| 3,054,800 A | 9/1962 | Burchfield et al. | 260/299 |
| 4,300,962 A | 11/1981 | Stinecipher et al. | 149/47 |
| 5,256,792 A | 10/1993 | Lee et al. | 548/263.8 |

OTHER PUBLICATIONS

Shevelev, S.A. et al., Russ. Chem. Bull., 1993, 42, 1063.
Junssen, et al, J. Org, Chem., 1973, 38, 1777.
Huttel, R., Chem. Ber., 1955, 88, 1586.

*Primary Examiner*—Joseph K. McKane
*Assistant Examiner*—Andrea D. Small
(74) *Attorney, Agent, or Firm*—Mark Homer

(57) ABSTRACT

Dinitropyrazolopyrazole-amine salts are used as burn modifier ingredients in gun propellant compositions.

13 Claims, 3 Drawing Sheets

DNPP Monoanion  DNPP dianion

| Compound | ΔHf (gas) (Kcal/mol) | ρ (g/cc) | Mol. Wt. | Formula | $I_{SP}$ (sec) | $D_V$ (mm/μsec) | $D_P$ (Kbar) | Impetus (J/g) | Flame Temp | $C_P/C_V$ |
|---|---|---|---|---|---|---|---|---|---|---|
| TAGN | -11.47 | 1.59 | 167.13 | $CH_9N_7O_3$ | 230.26 | 5.80 | 139.30 | 1157.83 | 2598.70 | 1.26 |
| DNPP-TAG | 240.49 | 1.82 | 302.21 | $C_5H_{10}N_{12}O_4$ | 265.42 | 9.53 | 372.90 | 1442.42 | 3522.60 | 1.24 |
| DNPP-AG | 199.78 | 1.80 | 272.19 | $C_5H_8N_{10}O_4$ | 248.63 | 8.80 | 326.00 | 1245.57 | 3179.70 | 1.26 |
| DNPP-G | 176.78 | 1.79 | 257.17 | $C_5H_7N_9O_4$ | 244.60 | 8.60 | 310.70 | 1194.04 | 3119.60 | 1.26 |
| DNPP-Hz | 171.78 | 1.81 | 230.14 | $C_4H_6N_8O_4$ | 274.08 | 9.08 | 357.30 | 1621.03 | 4142.90 | 1.26 |
| DNPP-AG2 | 241.42 | 1.74 | 346.27 | $C_6H_{14}N_{14}O_4$ | 251.63 | 9.24 | 324.40 | 1238.48 | 2945.50 | 1.23 |
| DNPP-G2 | 195.42 | 1.72 | 316.24 | $C_6H_{12}N_{12}O_4$ | 245.53 | 8.82 | 291.60 | 1186.77 | 2898.20 | 1.23 |
| DNPP-AT2 | 321.57 | 1.69 | 366.26 | $C_8H_{10}N_{14}O_4$ | 258.04 | 8.36 | 266.90 | 1186.63 | 3296.30 | 1.21 |

FIG. 3

DINITROPYRAZOLOPYRAZOLE-AMINE SALTS USEFUL IN GUN PROPELLANTS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention provides novel dinitropyrazolopyrazole-amine salts useful as burn rate modifier ingredients in gun propellants.

2. Brief Description of the Related Art

U.S. Pat. No. 5,256,792 to Lee et al. discloses a defined group of amine salts. However, these amine salts are limited in their energetic potential, positive heats of formation and densities.

There is a need in the art to provide a new energetic materials to improve gun propellant formulations The present invention addresses this and other needs.

SUMMARY OF THE INVENTION

The present invention includes a salt composition having a salt comprising a dinitropyrazolopyrazole anion (or dianion) and an amine cation(s). Preferred amine cations include guanidine, methylamine, methyl hydrazine, ethanolamine, 1,2,3-triaminopropane, aziridine, diethylenetriamine, 1,4-diaminobutane, pentaerythrityltetramine, biguanidine, biguanide, aminotriazole, 3,4,5-triamino-1,2,4-triazole, aminoguanidine, diaminoguanidine, triaminoguanidine, hydrazine and combinations thereof. The dinitropyrazolopyrazole anion may include either a mono-anion or di-anion structure to form one or more salts thereof.

The salts of the present invention are particularly useful in gun propellant compositions. As such the present invention also includes a burning gun propellant product produced by the process comprising the step of providing a gun propellant composition containing a salt comprising a dinitropyrazolopyrazole anion and an amine cation and initiating burn of said gun propellant.

DETAILED DESCRIPTION OF THE PREFERRED EMBODIMENT

The present invention provides for novel energetic compounds that include the salt of a dinitropyrazolopyrazole anion and an amine cation useful in gun propellants. These novel compounds provide flame temperature suppressants and burning-rate tailoring agents for the gun propellant, which are believed to result from the incorporation of certain nitrogen heterocycles and cationic amine countercations that modify the burning rates of the propellants.

Figure 1:
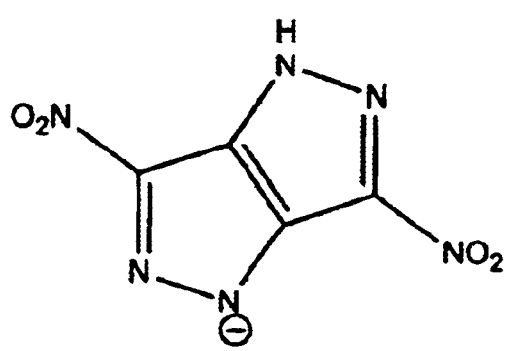
FIG. 1 illustrates the general structure of the DNPP mono-anion and DNPP dianion useful in the present invention.
Figure 1:
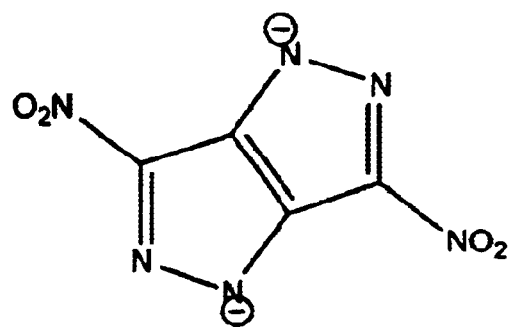

As seen in FIG. 1, the salt composition of the present invention includes the mono-anion and/or di-anion salt of dinitropyrazolopyrazole, also referred to as DNPP, with one or two amine cations. Use of the DNPP provides a platform for imparting specialized properties into the gun propellant by varying the cation component of the salt. As such the DNPP may constitute a mono-anion structure or di-anion structure of a singular amine cation. Additionally, the DNPP may include a di-anion structure of two distinct amine cations. These mono-anion and di-anion structures may be mixed within a gun propellant composition with other types of mono-anion and di-anion structures to form the gun propellant for tailoring the gun propellant composition for given characteristics. However, the close proximity of the two amine cations to the DNPP in the di-anion structure provides the most intimate mixture of the DNPP and amine. Accordingly, the salt may comprise at least one mono-anion, at least one di-anion, or combinations thereof. Combinations include two or more mono-anion salts, two or more di-anion salts, combinations of mono-anion salts and di-anion salts, etc.

Preferably the salt of the present invention includes a amine cation, either as a mono-anion or di-anion of the DNPP, such as aminoguanidine, aminotriazole, aziridine, biguanidine, biguanide, diaminoguanidine, diethylaenetriamine, ethanolamine, guanidine, hydrazine, methylamine, methyl hydrazine, pentaerythrityltetramine, triaminoguanidine, 1,2,3-triaminopropane, 1,4-diamninobutane, 3,4,5-triamino-1,2,4-triazole, and combinations thereof.

Figure 2:
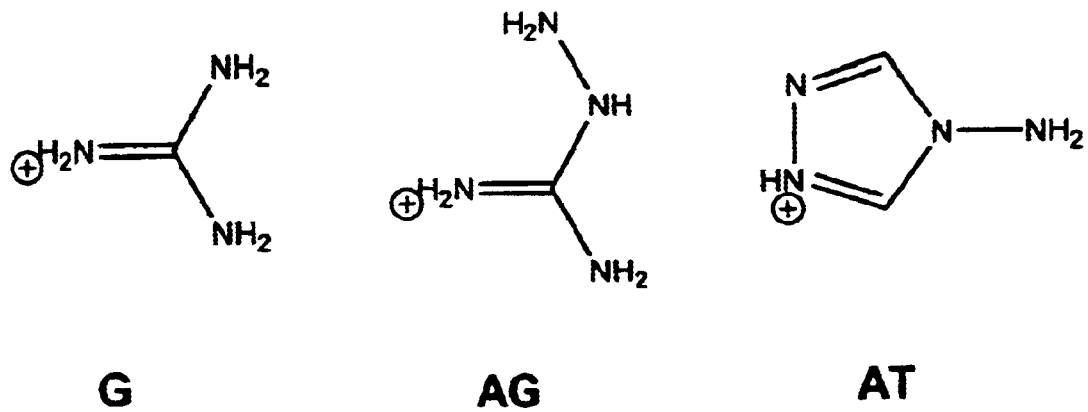
FIG. 2 illustrates the amine cations of guanidine (G), aminoguanidine (AG), aminotriazole (AT), hydrazine (HZ), diaminoguanidine (DAG) and triaminoguanidine (TAG) for combination with the DNPP mono-anion or dianion of the present invention; and, FIG. 3 is a comparative table of the calculated energetic properties of salts of the present invention and TAGN.
Figure 2:
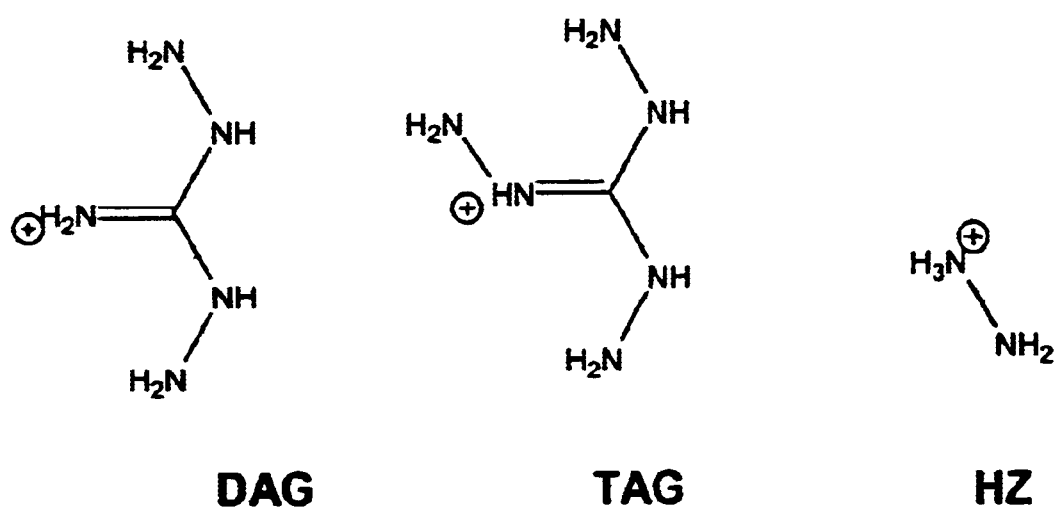

FIG. 2 illustrates a preferred group of dinitropyrazolopyrazole-amine salts of the present invention. These salts include the mono- or di-anion DNPP salts of hydrazine-dinitropyrazolopyrazole (HZ-DNPP and HZ2-DNPP, respectively), guanidine-dinitropyrazolopyrazole (G-DNPP and G2-DNPP, respectively), aminoguanidine-dinitropyrazolopyrazole (AG-DNPP and AG2-DNPP, respectively), diaminoguanidine-dinitropyrazolopyrazole (DAG-DNPP and DAG2-DNPP, respectively), triaminoguanidine-dinitropyrazolopyrazole (TAG-DNPP and TAG2-DNPP, respectively) and aminotriazole-dinitropyrazolopyrazole (AT-DNPP and AT2-DNPP, respectively). Most preferably the amine cation comprises either TAG-DNPP or HZ-DNPP.

FIG. 3 is a comparative table of the gun propellant characteristics of the salts of the present invention with other salts. As seen in FIG. 3, the DNPP-amine salts generally provide a higher $\Delta Hf$, impetus and nitrogen content than the corresponding dinitropyrazole (DNP) salts. As such, the DNPP-amine salts promote desirable characteristics into a formed gun propellant composition.

As detailed in the examples below, formation of the DNPP-amine salts occurs with the reaction of the dinitropyrazolopyrazole with the amine, which is removed as a formed precipitate. Any appropriate solvent may be used, with the selection of solvent determinable by one skilled in the art. The preferred solvent comprises water. NaOH, MeOH, KOH and like basic compounds may be used to deprotonate amine salts which thereby generates a free base solution. The resultant basic amine can then react with DNPP to form a salt. Recrystallization may be done as desired, particularly for increasing the purity of the resulting precipitate, with recrystallization preferably occurring in water.

Formation of the di-anion of DNPP occurs with the addition of 2:1 molar ratio amine to DNPP, respectively. In the di-anion DNPP structures, shown in FIG. 1, amine cation A may be the same or different than amine cation B. Although deprotonation of DNPP with a second amine theoretically becomes more difficult than the addition of the first amine as the negative charge of the DNPP at the second site becomes partially dissipated once the first amine cation has formed from deprotonation of DNPP, the equilibrium for the salt complex to form remains favored over non-formation. Accordingly the formation of the mono-anion DNPP reacts to completion prior to the formation of the di-anion DNPP for a given amine reactant. With additional amine, i.e., above a 1:1 molar ratio to the DNPP, the di-anion DNPP forms.

The following examples exemplify certain preferred embodiments of the present invention. Melting points were uncorrected. $^1H$ and $^{13}C$ NMR spectra were obtained in DMSO-$D_6$ at 200 and 50 MHz, respectively, on a Varian VXR-200 Mhz NMR spectrometer. Chemical shifts are referenced to residual H in perdeuterated solvents ($\delta$ 2.500, DMSO-$D_6$). IR spectral were recorded on a Perkin Elmer 1600 FTIR spectrometer.

EXAMPLE 1

Triaminoguanidinium 3,6-Dinitropyrazolo(4,3-c)pyrazole (TAG-DNPP Salt)

Solid triaminoguanidinium nitrate (TAGN; 928 mg, 5.55 mmol) was added in one portion at room temperature to a stirred yellow solution of 3,6-dinitropyrazolo(4,3-c) pyrazole (DNPP; 1.0 g, 5.04 mmol), NaOH (202 mg, 5.04 mmol), and deionized $H_2O$ (60 mL). The solution was stirred 2 hours at room temperature, was cooled to about 10° C., and the resultant precipitate was filtered and washed with cold $H_2O$ to give a yellow solid (1.39 g, 91%). Recyrstallization from $H_2O$ gave TAG-DNPP monohydrate salt as yellow crystals. The anhydrous salt was obtained by heating (90° C.) the hydrate under vacuum for 2 hours to give yellow crystals. mp: 205° C. (dec). IR(KBr) 3320 (s), 1685 (s), 1340 (s), 1235 (s), 1135 (s) cm$^{-1}$. $^1H$ NMR (200 MHz) $\delta$ 13.8 (b, 1H, DNPP-H), 8.592 (s, 3H, TAG N—H) 4.489 (s, 6H, TAG N—NH$_2$). $^{13}C$ NMR (50 MHz) $\delta$ 158.916, 139.364, 137.041. Anal. Calcd for $C_5H_{10}N_{12}O_4$: C, 19.87; H, 3.34; N, 55.62. Found: C, 19.69; H, 3.35; N, 54.68.

EXAMPLE 2

Mono-aminoguanidinium 3,6-Dinitropyrazolo(4,3-c)pyrazole (AG-DNPP Salt)

Aminoguanidine bicarbonate (0.7 g, 5.1 mmol) was added in one portion to a solution of DNPP(1 g, 5 mmol) and NaOH (0.21 g, 5.1 mmol) in 20 mL of $H_2O$ solution. A yellow slurry formed upon addition. The slurry was allowed to stir at room temperature overnight. The precipitate was collected by suction filtration and washed with EtOH to yield a yellow powder. (1.15 g, 84%) Recrystallization from $H_2O$ (15 mL) yielded yellow-orange matted needles (0.84 g. 62%); m.p. 174–178° C. (The material shrinks and turns orange before melting);IR(KBr)3450, 3355, 3297, 3264, 3169, 1673, 1658, 1633, 1534, 1501, 1442, 1382, 1344, 1238, 1126, 1103, 1030, 877, 827, 785, 755 cm$^{-1}$.

EXAMPLE 3

Bis-aminoguanidinium 3,6-Dinitropyrazolo(4,3-c)pyrazole (AG2-DNPP Salt)

A solution of aminoguanidine carbonate (1.44 g, 10.6 mmol) in 15 mL of $H_2O$ was neutralized with NaOH to yield a white slurry. This was added to a solution of DNPP (1 g, 5 mmol) in a MeOH/$H_2O$ solution (2:1, 12 mL). An orange slurry formed upon addition which was allowed to stir at room temperature overnight. The precipitate was collected by suction filtration and washed with EtOH to yield a light orange powder. (1.70 g, 99%) Recrystallization from 1:1 MeOH/$H_2O$ yielded yellow-orange matted needles; m.p. 181° C.; IR(KBr)3548, 3446, 3409, 3348, 3218, 3163, 3050, 1681, 1654, 1462, 1432, 1370, 1295, 1229, 1207, 1080, 956, 831 cm$^{-1}$.

EXAMPLE 4

Mono-guanidinium 3,6-Dinitropyrazolo(4,3-c)pyrazole (G-DNPP Salt)

Guanidine nitrate (0.65 g, 5.1 mmol) was added in one portion to a solution of DNPP(1 g, 5 mmol) and NaOH (0.21 g, 5.04 mmol) in 20 mL of $H_2O$ solution. A thick, orange slurry formed upon addition, 10 mL of water was added and the mixture was allowed to stir at room temperature overnight. The precipitate was collected by suction filtration and washed with EtOH to yield an orange powder. Recrystallization from $H_2O$ (15 mL) yielded yellow needles; 0.78 g(62%); m.p. 301–302° C.; IR(KBr)3619, 3460, 3364, 3293, 3219, 2793, 1667, 1493, 1454, 1374, 1344, 1240, 1115, 1035, 885, 826 cm$^{-1}$. Reducing the volume of the filtrate yielded a second crop (0.08 g).

EXAMPLE 5

Bis-guanidinium 3,6-Dinitropyrazolo(4,3-c)pyrazole (G2-DNPP Salt)

Guanidine nitrate (1.35 g, 11 mmol) was added in one portion to a solution of DNPP(1 g, 5 mmol) and NaOH (0.41 g, 10.8 mmol) in 20 mL of $H_2O$ solution. A thick, orange slurry formed upon addition, 10 mL of water was added and the mixture was allowed to stir at room temperature overnight. The precipitate was collected by suction filtration and washed with EtOH to yield an orange powder (1.41 g, 90%). Recrystallization from $H_2O$ (150 mL) yielded red-orange matted needles (1.25 g. 80%); m.p. 319–320° C. (the material shrinks before melting); IR(KBr) 3455, 3425, 3364, 3282, 3146, 3017, 2801, 1653 1458, 1413, 1361, 1265, 1220, 1070, 1054, 748 cm$^{-1}$.

EXAMPLE 6

Bis-(4-amino-1,2-triazole) Salt of 3,6-Dinitropyrazolo(4,3-c)pyrazole (AT2-DNPP Salt)

DNPP (1 g, 5.04 mmol) was suspended in 10 mL of MeOH and 4 mL of $H_2O$. To this was added 4-amino-1,2,4-triazole (0.90 g, 10.6 mmol) and the mixture was brought to reflux, cooled and allowed to stir at room temperature for 4 hours. The resulting yellow precipitate was collected by suction filtration and washed with EtOH to yield a yellow powder (1.67 g, 86%). Recrystallization from water (20 mL) yielded yellow microcrystals; m.p. 217–220° C.; IR(KBr) 3599, 3511, 3341, 3138, 3084 2816, 2762, 2694, 1610, 1523, 1384, 1368, 1351, 1244, 1039, 1014, 984, 827 cm$^{-1}$.

EXAMPLE 7 (PROPHETIC)

Bis-Triaminoguanidinium 3,6-Dinitropyrazolo(4,3-c)pyrazole (TAG2-DNPP Salt)

Solid triaminoguanidinium nitrate (TAGN; 1856 mg, 11.10 mmol) is added in one portion at room temperature to a stirred yellow solution of 3,6-dinitropyrazolo(4,3-c) pyrazole (DNPP; 1.0 g, 5.04 mmol), NaOH (202 mg, 5.04 mmol), and deionized $H_2O$ (60 mL). The solution is stirred 2 hours at room temperature, is cooled to about 10° C., and the resultant precipitate is filtered and washed with cold $H_2O$ to give a yellow solid (1.39 g, 91%). Recyrstallization si done in an $H_2O$ solution. The anhydrous salt is obtained by heating (90° C.) the hydrate under vacuum for 2 hours to give yellow crystals.

EXAMPLE 8 (PROPHETIC)

Mono-(4-amino-1,2,4-triazole) Salt of 3,6-Dinitropyrazolo(4,3-c)pyrazole (AT-DNPP Salt)

DNPP (1 g, 5.04 mmol) is suspended in 10 mL of MeOH and 4 mL of $H_2O$. To this is added 4-amino-1,2,4-triazole (0.45 g, 5.3 mmol) and the mixture is brought to reflux, cooled and allowed to stir at room temperature for 4 hours. The resulting yellow precipitate is collected by suction filtration and washed with EtOH to yield a yellow powder. Recrystallization from water (20 mL) yields yellow microcrystals.

Mono-hydrazine 3,6-dinitropyrazolo(4,3-c)pyrazole (HZ-DNPP salt), bis-hydrazine 3,6-dinitropyrazolo(4,3-c) pyrazole (HZ2-DNPP salt), mono-diaminoguanidine 3,6-dinitropyrazolo(4,3-c) pyrazole (DAG-DNPP salt) and bis-diaminoguanidine 3,6-dinitropyrazolo(4,3-c) pyrazole (DAG2-DNPP salt) are similarly made from the reaction of hydrazine or diaminoguanidine compound with the DNPP in the appropriate ratios, such as a 1:1 molar ratio for the DNPP monoanion and a 1:2 (DNPP:amine) molar ratio for the DNPP dianion resultant.

The dinitropyrazolopyrazole-amine salts are useful as components in new gun propellant compositions. When incorporated into the gun propellant, the DNPP-amine salts burn with distinct properties. Combustion intermediates of the salts provide a basis for flame temperature suppressants and burning-rate tailoring agents, with the creation of endothermically formed CHNO oligomers upon pyrolysis. Additionally, lower flame temperatures may be enhanced with nitrogen formation of the counterions of the amine component of the dinitropyrazolopyrazole-amine salts. With the initiation of gun propellant burning, the resultant burnt gun propellant may impart particular advantages to the gun firing.

The foregoing summary, description, and examples of the present invention are not intended to be limiting, but are only exemplary of the inventive features which are defined in the claims.

What is claimed is:

1. A salt composition having a salt comprising:

at least one dinitropyrazolopyrazole anion, wherein the dinitropyrazolopyrazole is selected from a mono-anion, a di-anion, or a combination thereof; and, at least one amine cation.

2. The salt of claim 1, wherein the at least one amine cation is selected from the group consisting of aminoguanidine, aminotriazole, aziridine, biguanidine, biguanide, diaminoguanidine, diethylaenetriamine, ethanolamine, guanidine, hydrazine, methylamine, methyl hydrazine, pentaerythrityltetramine, triaminoguanidine, 1,2,3-triaminopropane, 1,4-diaminobutane, 3,4,5-triamino-1,2,4-triazole, and combinations thereof.

3. The salt of claim 1, wherein the salt comprises at least one dinitropyrazolopyrazole mono-anion.

4. The salt of claim 1, wherein the salt comprises at least one dinitropyrazolopyrazole di-anion.

5. The salt of claim 3, wherein the salt comprises a combination of two or more mono-anion salts.

6. The salt of claim 4, wherein the salt comprises a combination of two or more di-anion salts.

7. The salt of claim 1, wherein the salt comprises a combination of one or more mono-anion salts and one or more di-anion salts.

8. The salt of claim 1, wherein the salt comprises one or two hydrazine cations.

9. The salt of claim 1, wherein the salt comprises one or two guanidine cations.

10. The salt of claim 1, wherein the salt comprises one or two aminoguanidine cations.

11. The salt of claim 1, wherein the salt comprises one or two diaminoguanidine cations.

12. The salt of claim 1, wherein the salt comprises one or two triaminoguanidine cations.

13. The salt of claim 1, wherein the salt comprises one or two aminotriazole cations.

* * * * *